United States Patent [19]
Colvin, Jr.

[11] Patent Number: 5,517,313
[45] Date of Patent: May 14, 1996

[54] FLUORESCENT OPTICAL SENSOR

[76] Inventor: Arthur E. Colvin, Jr., 4155 Baltimore, Mount Airy, Md. 21771

[21] Appl. No.: 393,166

[22] Filed: Feb. 21, 1995

[51] Int. Cl.⁶ .................................................. G01N 21/25
[52] U.S. Cl. .................. 356/417; 422/82.07; 250/458.1; 436/172
[58] Field of Search .................................. 356/416, 417, 356/39, 246, 437, 317–318; 250/364, 365, 458.1, 459.1, 461.1, 461.2; 128/633.01, 634; 436/172, 68, 163, 169, 178; 422/83, 68.1, 52, 83, 91, 82.06, 82.07, 82.08

[56] References Cited

U.S. PATENT DOCUMENTS

| | | | |
|---|---|---|---|
| 4,003,707 | 1/1977 | Lubbers et al. | 356/39 X |
| 4,084,905 | 4/1978 | Schreiber et al. | 356/317 |
| 4,643,877 | 2/1987 | Opitz et al. | 356/417 X |

Primary Examiner—Vincent P. McGraw
Assistant Examiner—K. P. Hantis
Attorney, Agent, or Firm—Michael W. York

[57] ABSTRACT

A fluorescence sensor for detecting the presence and amount of an analyte. The fluorescence sensor has a photodetector, a high pass filter located adjacent the photodetector, and a glass layer located adjacent the high pass filter. An indicator layer is located adjacent the glass layer and a light emitting diode is embedded in the indicator layer. The indicator layer has indicator molecules that provide a fluorescent emission as a result of light from the light emitting diode. The indicator layer also allows an analyte to diffuse into it and the presence of the analyte reduces the amount of light emitted from the indicator molecules that passes through the glass layer and the high pass filter and is incident upon the photodetector. Since the amount of current from the photodetector depends upon the incident light, this is used to detect the presence and amount of the analyte. In one embodiment a waveguide is also present.

19 Claims, 4 Drawing Sheets

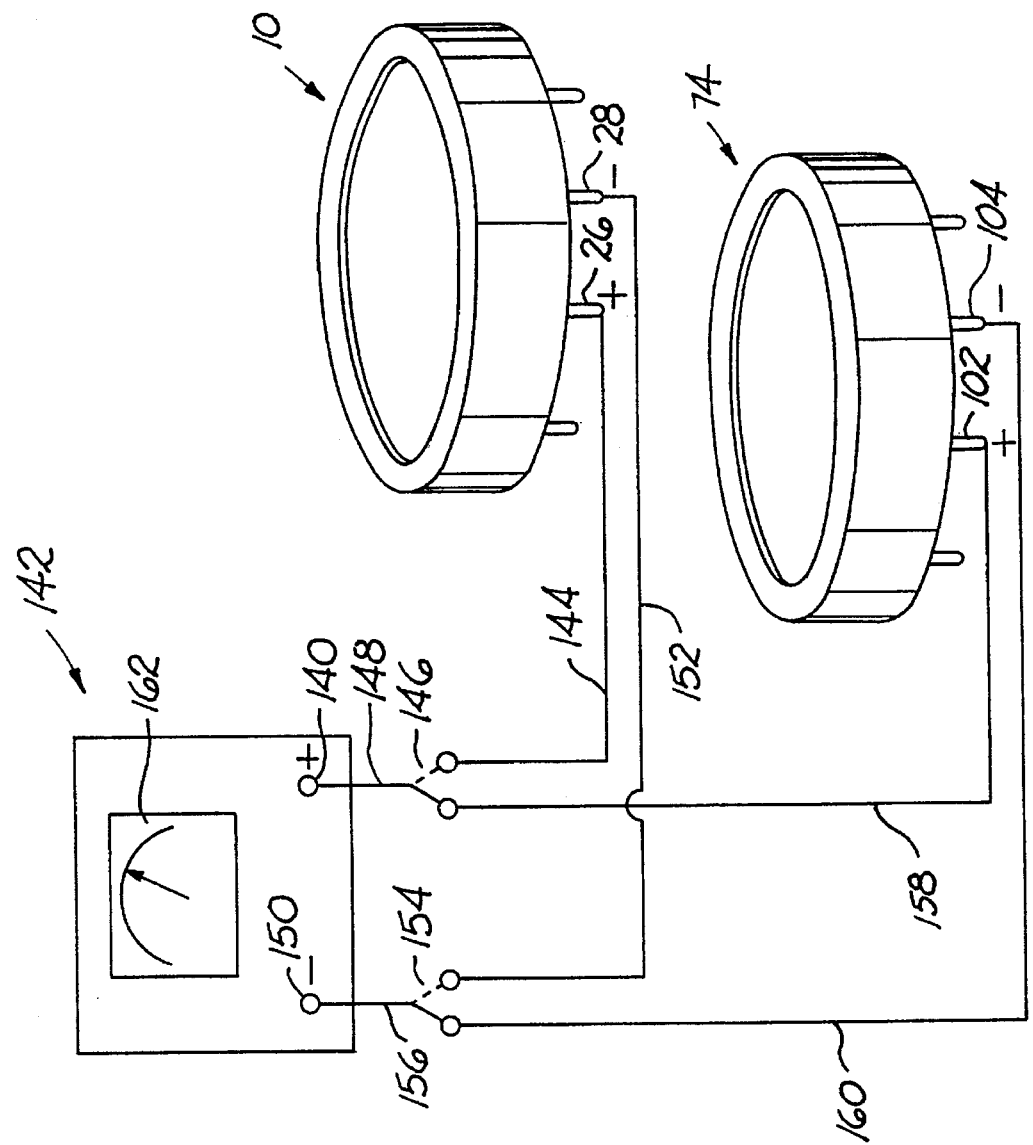

FLUORESCENT OPTICAL SENSOR

BACKGROUND OF THE INVENTION

Fluorescence is a photochemical phenomena in which a photon of specific light wavelength (excitation wavelength) strikes an indicator molecule, thereby exciting an electron to a higher energy state as a result of the collision. As that "excited" electron decays back down to its original ground state, another photon of light is released at a longer wavelength (emission wavelength).

Indicator molecules are specific in their excitation and emission wavelengths. The fluorescent emission from an indicator molecule may be attenuated or enhanced by the local presence of the molecule being analyzed. For example, a tris(4,7-diphenyl-1,10-phenanthroline)ruthenium (II) perchlorate molecule particular for oxygen sensing is excited by shining light onto the substance at 460 nm (blue). The molecules' fluorescent emission immediately occurs at 620 nm (orange-red). However, the emission is quenched by the local presence of oxygen interacting with the indicator molecule, to cause the intensity of the fluorescence to be related to the ambient oxygen concentration. Consequently, the more oxygen that is present, the lower the emission intensity and vice-versa and when zero or no oxygen is present, the maximum fluorescent intensity of emitted light is present.

These analytical techniques using fluorescent molecules as indicators have classically been used in fluorescence spectrophotometers. These instruments are designed to read fluorescence intensity and also the decay time of fluorescence. These devices typically cost 20,000 to 50,000 dollars and are used generally in research laboratories.

A second area of fluorescence sensor state-of-the-art is in fiber optic devices. These sensor devices allow miniaturization and remote sensing of specific analytes. The fluorescent indicator molecule is immobilized via mechanical means or chemistry to one end of an optical fiber. To the opposite end of the fiber is attached a fiber coupler (Y shaped fiber) or a beam splitter.

Incident excitation light is coupled into one leg of the fiber typically via a filtennd a lens. Excitation light is carried via the fiber to the distal end where the fluorescent indicator molecule is immobilized to the tip. Upon excitation, the indicator molecule uniformly radiates the fluorescent light, some of which is recaptured by the fiber tip and propagated back through the fiber to the Y junction or "coupler". At the junction, a substantial portion (typically half) of the fluorescence is conveyed back to the emitter or point of origin thereby unavailable for signal detection. To offset the inefficiencies of the system, lasers are often used to raise the input power and highly sensitive photomultiplier tubes are used as detectors thereby raising costs by thousands of dollars. The other half travels along the other leg of the Y to the detector and is recorded. A primary disadvantage with the system is the losses occurring at each fiber junction and via lenses and filters. The system is at a maximum 1–5% efficient with resultant loss in sensitivity and range. These devices have been demonstrated in the lab and are very recently available commercially for very limited applications. These devices differ from the previously mentioned fluorescence spectrophotometers in that they are dedicated to their specific application.

In view of the foregoing it is readily apparent that there are definite limitations associated with such prior art fluorescence devices including cost inefficiency and limitations related to use. In addition, such prior art fluorescence devices are complex with many separate parts and are bulky.

This invention overcomes these problems associated with prior fluorescence devices and provides a fluorescence device with greatly reduced costs and complexity as well as greatly improved efficiency. This invention provides a novel platform which greatly extends the use of fluorescent indicator molecules as a sensor allowing utilization, sensitivity and cost analyses not previously available. The invention also has increased uses and is easier to use as well as being more reliable than prior art fluorescence devices.

SUMMARY OF THE INVENTION

This invention relates to the fluorescence devices and more particularly to fluorescence sensors.

Accordingly, it is an object of the invention to provide an improved fluorescence sensor.

It is an object of the invention to provide a fluorescence sensor that is highly efficient.

It is an object of the invention to provide a fluorescence sensor with improved optical efficiency.

It is an object of the invention to provide a fluorescence sensor that has increased sensitivity.

It is an object of the invention to provide a fluorescence sensor that has few parts.

It is an object of the invention to provide a fluorescence sensor that is easy to manufacture.

It is an object of the invention to provide a fluorescence sensor that has greatly reduced manufacturing costs.

It is an object of the invention to provide a fluorescence sensor that is manufactured with standard manufacturing techniques.

It is an object of the invention to provide a fluorescence sensor that is easy to assemble.

It is an object of the invention to provide a fluorescence sensor that is low in cost.

It is an object of the invention to provide a fluorescence sensor that has an increased number of uses.

It is an object of the invention to provide a fluorescence sensor that can be used in harsh environments.

It is an object of the invention to provide a fluorescence sensor that has increased thermal tolerances.

It is an object of the invention to provide a fluorescence sensor that is miniaturized.

It is an object of the invention to provide a fluorescence sensor with reduced volume.

It is an object of the invention to provide a fluorescence sensor that provides increased functionality with reduced volume.

It is an object of the invention to provide a fluorescence sensor with increased functional density.

It is an object of the invention to provide a fluorescence sensor that is well suited for use in places where the volume available is limited.

It is an object of the invention to provide a fluorescence sensor that is well suited for use in a variety of difficult situations.

It is an object of the invention to provide a fluorescence sensor that includes an emitter element that is imbedded within a chemically active element.

It is an object of the invention to provide a fluorescence sensor that includes an emitter element that is imbedded within a polymer (organic or inorganic) within which the indicator molecule is immobilized.

It is an object of the invention to provide a fluorescence sensor which may be used as a platform for fluorescent, luminescent, phosphorescent, absorbent or refractive difference indicator molecules immobilized on or within the polymer in which the emitter is imbedded.

It is an object of the invention to provide a fluorescence sensor with an imbedded emitter whereby the technique of querying the indicator molecule is via direct excitation/emission, evanescent excitation, or surface plasmon resonance type excitation or indirect excitation via a secondary fluorescent molecule.

It is an object of the invention to provide a fluorescence sensor where the emission element that is embedded is integral with low and high pass optical filters.

It is an object of the invention to provide a fluorescence sensor that has an integral optical detection element or diode.

It is an object of the invention to provide a fluorescence sensor which is built in one piece unit substantially on a single chip or integral package.

It is an object of the invention to provide a fluorescence sensor in which all optical processing is contained within the integral component and only power and signal leads enter and exit the active device or unit.

It is an object of the invention to provide a fluorescence sensor where the emitter enclosed is a light emitting diode (LED) die so as to provide optimal radial emission of excitation radiation from the source.

It is an object of the invention to provide a fluorescence sensor where the primary axis of excitation radiation from a light emitting diode is perpendicular to the primary axis of the photodetection of the emission of the photodetector.

It is an object of the invention to provide a fluorescence sensor that eliminates the need for fiber optics.

It is an object of the invention to provide a fluorescence sensor with a unitary structure where the entire radiation of the light source is initially released and propagated through the indicator layer, either within the layer or immobilized to the surface of the layer.

It is an object of the invention to provide a fluorescence sensor which may be used in analysis of gaseous or liquid states.

It is an object of the invention to provide a fluorescence sensor which may be used integral with its signal processing electronics or as a remote device.

It is an object of the invention to provide a fluorescence sensor where the membrane or indicator layer thickness is controlled by pouring the formulated contents by gravity or pressure around the emitter die.

It is an object of the invention to provide a fluorescence sensor where the thickness of the indicator layer is optically limited only by the thickness of the radially emitting P/N junction.

It is an object of the invention to provide a fluorescence sensor which has a low pass filter that is a coating or film.

It is an object of the invention to provide a fluorescence sensor which has a high pass filter that is a coating, film, or wafer.

It is an object of the invention to provide a fluorescence sensor which may be used for a multitude of analytes by immobilizing a specific indicator molecule on or within the sensor's indicator layer and calibrating the signal processing electronics.

It is an object of the invention to provide a fluorescence sensor whose signal processing electronics may include phase modulation, lifetime, intensity or relative intensity data interpretation methods.

It is an object of the invention to provide a fluorescence sensor which may have any emission wavelengths and any detection wavelengths.

It is an object of the invention to provide a fluorescence sensor where the low and high pass filters may be of any suitable exclusion/admission profile suitable to the indicator molecules chosen.

It is an object of the invention to provide a fluorescence sensor where the sensor is a solid state sensor.

It is an object of the invention to provide a fluorescence sensor which is designed for extremes of temperature, pressure and ambient conditions.

These and other objects will be apparent from the fluorescence sensor invention that has a photodetector, a high pass filter located adjacent the photodetector, and a glass layer located adjacent the high pass filter. Also, an indicator layer is located adjacent to the glass layer and a light emitting diode is embedded in the indicator layer. The indicator layer has indicator molecules that provide a fluorescent emission as a result of light from the light emitting diode. The indicator layer allows an analyte to diffuse into it and the presence of the analyte alters the amount of light emitted from the indicator molecules that passes through the glass layer and the high pass filter and is incident upon the photodetector. Since the amount of current from the photodetector depends upon the incident light this is used to detect the presence and amount of the analyte. In one embodiment a waveguide is also present.

BRIEF DESCRIPTION OF THE DRAWINGS

The invention will be hereinafter more fully described with references to the accompanying drawings in which:

FIG. 6 is a perspective view of the embodiments of the fluorescence sensor invention in use with an indicator.

DETAILED DESCRIPTION OF THE PREFERRED EMBODIMENT

Figure 1:
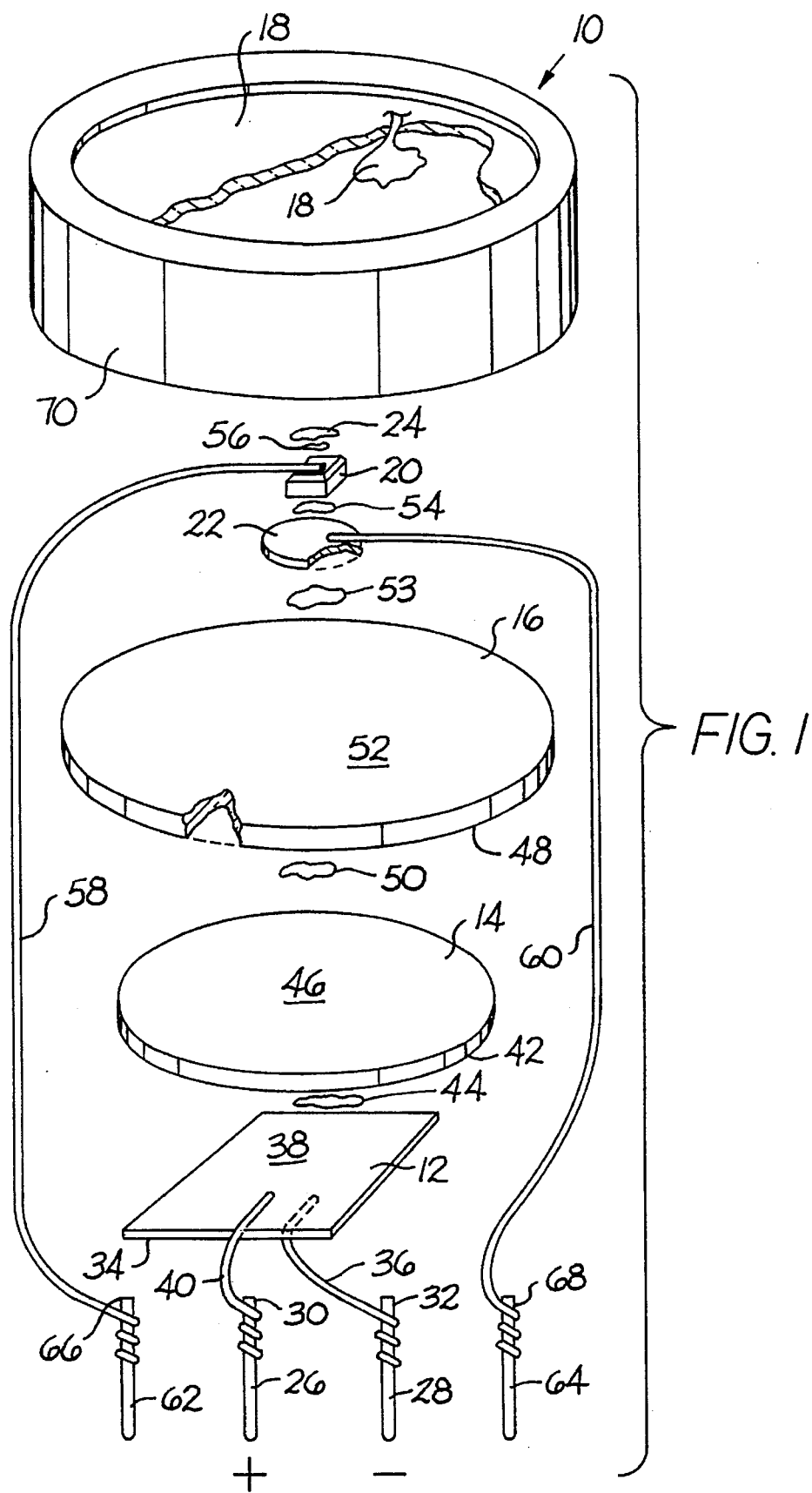
FIG. 1 is a perspective partially exploded view of the fluorescence sensor invention illustrating its component parts and how it is manufactured.
Figure 2:
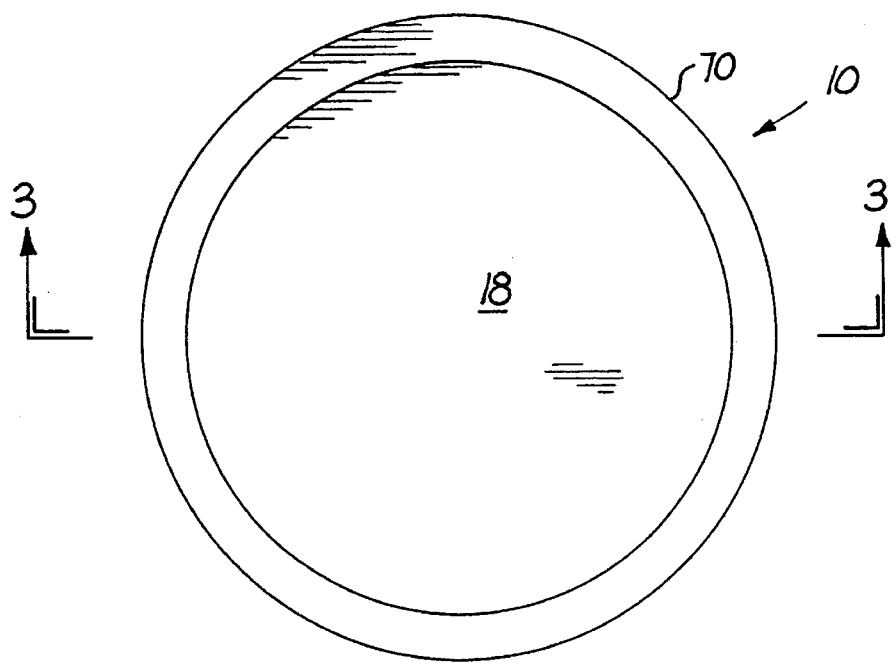
FIG. 2 is a top plan view of the fluorescence sensor invention set forth in FIG. 1.
Figure 3:
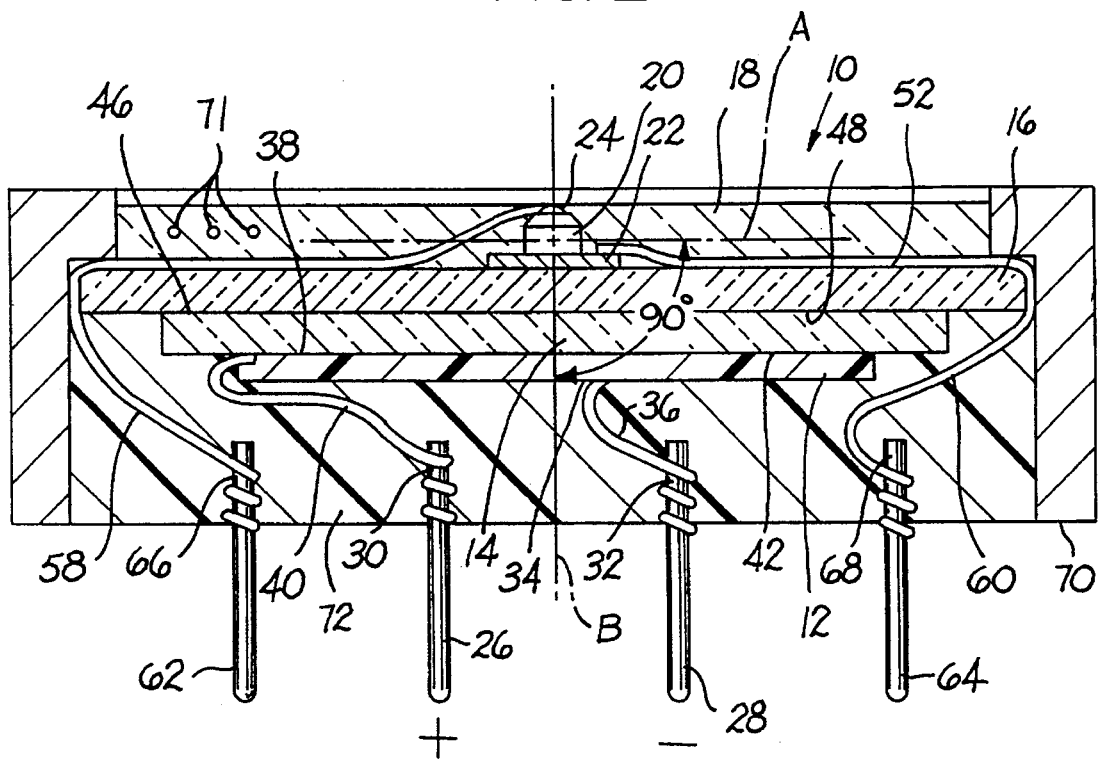
FIG. 3 is an enlarged sectional view of the of the fluorescence sensor invention set forth in FIGS. 1 and 2 taken substantially on the line 3—3 of FIG. 2.

Referring first to FIGS. 1, 2, and 3, the fluorescence sensor invention is illustrated and is designated generally by the number 10. The sensor 10 comprises photodetector means for detecting light comprising a thin substantially flat photodetector or wafer 12, filtering means for filtering light comprising a thin substantially flat high pass filter layer 14 that has a generally circular perimeter that is located adjacent to and is optically coupled to the photodetector means comprising the photodetector wafer 12 and a thin substantially flat glass wafer 16 that has a generally circular perimeter that is located adjacent to and is optically coupled to the filter means comprising the high pass filter layer 14. The sensor 10 also comprises indicator means for providing a fluorescent emission as a result of excitation light comprising a substantially flat thin indicator membrane layer 18 that has a generally circular perimeter that is located adjacent to and is optically coupled to the glass layer 16, light emitting means for emitting excitation light comprising a light emitting diode 20 (LED) that is located within the central portion of the indicator layer 18 and a thin electrically conductive reflective metal disc 22 that is located between the light emitting diode 20 and the glass wafer 16 plus filtering means for filtering light comprising a low pass filter coating 24 surrounding the upper portion of the light emitting diode 20. As indicated in FIG. 1, the indicator layer 18 is poured into place.

The details of the construction of the sensor 10 can best be understood by referring to FIG. 3 as well as FIG. 1. As illustrated in FIGS. 1 and 3, the photodetector layer 12 is connected to a positive post 26 and a negative post 28 whose respective upper end portions 30 and 32 are electrically connected to the photodetector layer 12. A lead 36 has one end soldered or secured by conductive adhesive to the upper end portion 30 of the post 26 and the other end is attached or secured in a conventional manner to the upper surface 38 of the photodetector layer 12. In a similar manner, a lead 40 has one end secured to the upper end portion 32 of the post 28 by soldering or by a conductive adhesive and the other end is secured or attached to the underside 34 of the photodetector 12 in a conventional manner.

The high pass filter layer 14 has its underside 42 secured to the upper side or surface 38 of the photodetector layer 12 by a very thin layer of optical adhesive 44 and the upper surface 46 of the high pass filter layer 14 is secured to the lower surface 48 of the glass layer 16 by another very thin layer of optical adhesive 50. The reflective foil 22 is attached to the upper surface 52 of the glass layer 16 by a suitable adhesive 53 known in the art and the light emitting diode 20 is attached to the upper surface of the reflective foil 22 by an electrically conducting adhesive layer 54. The low pass filter coating 24 is secured to the upper outer portion of the light emitting diode 20 by light conductive adhesive 56.

Electrical leads 58 and 60 are provided for the light emitting diode 20 and extend respectively from the light emitting diode 20 and the electrically connected conductive foil disc 22 to the respective upper end portions 66 and 68 of the posts 62 and 64 whose respective upper end portions 66 and 68 are located below the outer portion of the under surface 42 of the filter layer 14. The indicator membrane layer 18 contains indicator molecules designated by the number 71 and is cast onto the upper surface 52 of the glass layer 16 as well as around the light emitting diode 20 and its low pass filter coating 24 and portions of its leads 58 and 60.

Also, a circular ring shaped machined metal housing 70 is provided that circles the outer edges of the photodetector layer 12, the filter layer 14, the glass layer 16 and the membrane layer 18. The lower portion of the machined housing 70 is closed or sealed off with casting ceramic or other potting material 72 known in the art that also secures the posts 26, 28, 62 and 64 in place. Consequently, the sensor 10 is a unitary structure with all its operational components located within the housing 70 and only the positive and negative signal posts 26 and 28 and the electrical power posts 62 and 64 extending from the unitary structure surrounded by and contained within the housing 70. It is important to note, as indicated in FIG. 3, that the light emitting diode 20 and the photodetector 12 are located in such a manner that the primary or main axis of light emission from the light emitting diode 20, designated by the letter A, is substantially perpendicular to the primary or main axis, designated by the letter B, of light detection of the photodetector 12. This is very important for the fluorescence sensor 10 since it it results in high efficiency and high sensitivity.

Figure 4:
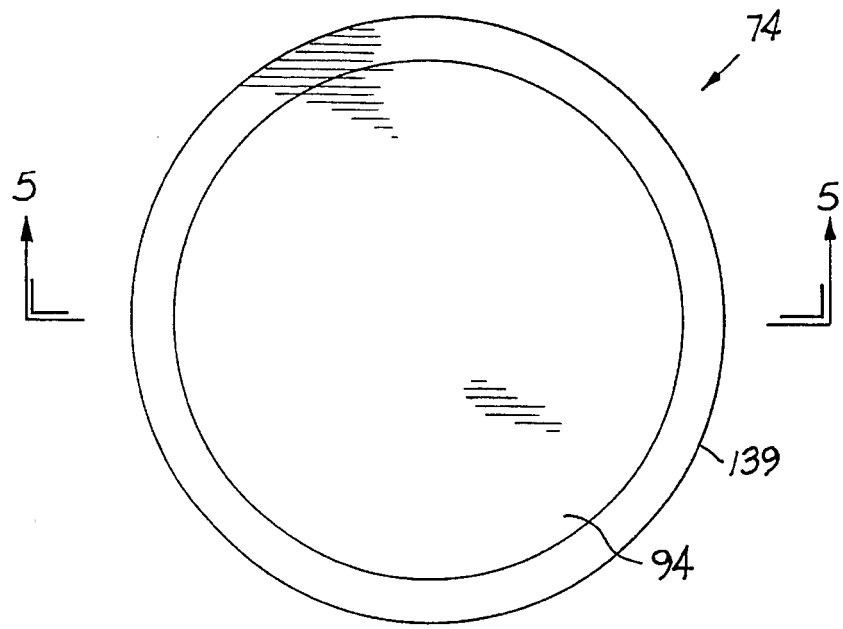
FIG. 4 is a top plan view of a second embodiment of the fluorescence sensor invention.
Figure 5:
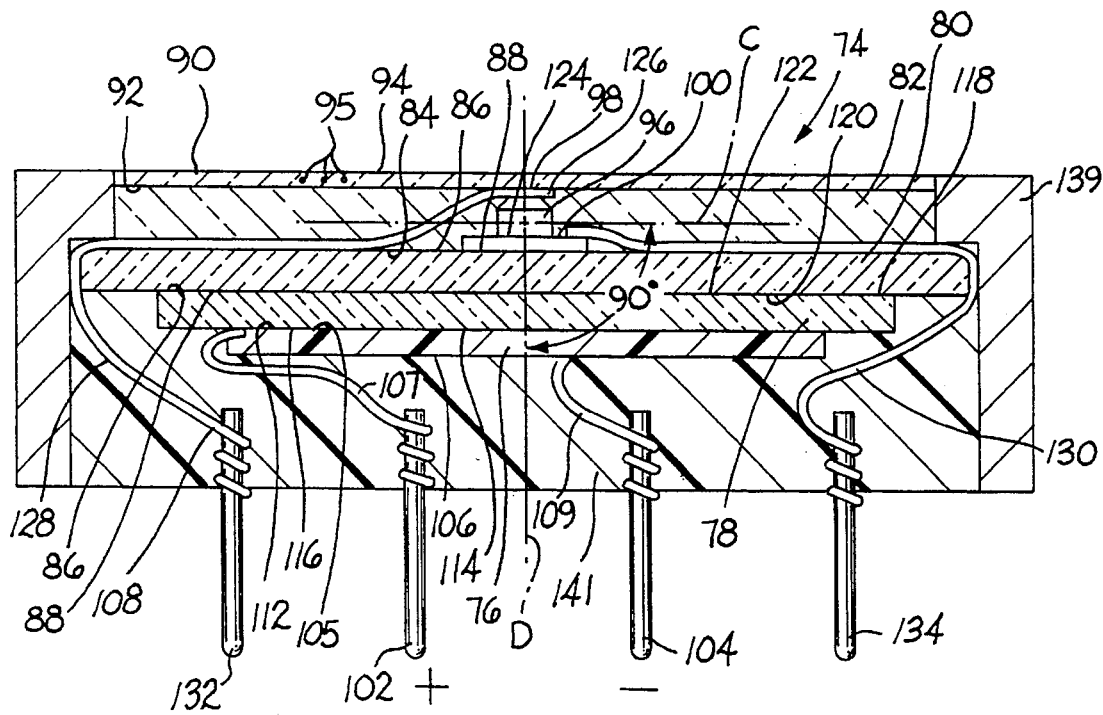
FIG. 5 is an enlarged sectional view of the fluorescence sensor invention set forth in FIG. 4 taken substantially on the line 5—5 of FIG. 4.

Another embodiment of the fluorescence sensor invention is set forth in FIGS. 4 and 5 and is designated generally by the number 74. The sensor 74 comprises photodetector means for detecting light comprising a thin photodetector layer 76 that is substantially identical to the previously described photodetector wafer or layer 12, filtering means for filtering light comprising a high pass filter layer 78 that is substantially identical to the previously described high pass filter layer 14 and a glass layer 80 that is substantially identical to the previously described glass layer 16. The high pass filter layer 78 is located adjacent to and is optically coupled to the photodetector means comprising the photodetector layer or wafer 76. The glass layer 80 is located adjacent to and is optically coupled to the filter means comprising the filter layer 78. However, the sensor 74 also has waveguide means for functioning as a waveguide comprising a thin substantially flat waveguide layer 82 whose under surface 84 is located adjacent to and is in optical contact with the upper surface 86 of the glass layer 80 as a result of optical adhesive 88. The upper surface 90 of the waveguide layer 82 is located adjacent to and is in optical contact with the lower surface 92 of an indicator layer 94. This indicator membrane layer 94 has indicator molecules designated by the number 95 and may be cast onto the upper surface 90 of the waveguide layer 82. The sensor 74 also has light emitting means for emitting excitation light comprising a light emitting diode 96 that is similar to the previously described diode 20, filtering means for filtering light comprising a low pass filter coating 98 surrounding the upper portions of the diode 96 that is similar to the previously described low pass filter coating 24 and the light emitting diode 96 has its lower surface in contact with a thin electrically conductive reflective metal foil disc 100 that is similar to the previously described reflective metal foil disc 22.

As illustrated in FIG. 5, the sensor 74 has respective positive and negative posts 102 and 104, that are similar to the previously described posts 26 and 28, and are electrically connected to the respective upperside 105 and underside 106 of the photodetector layer 76 in a conventional manner via the respective electrical leads 107 and 109. The high pass filter layer 78 has its lower surface 114 secured to the upper surface 112 of the photodetector layer 76 by a very thin layer of optical adhesive 116 similar to the previously described adhesive 44. The upper surface 118 of the high pass filter 78 is also secured to the lower surface 120 of the glass layer 80 by a thin layer 122 of optical adhesive similar to the previously described adhesive 50. The reflective foil disc 100 is connected to the upper surface 86 of the glass layer 80 by a suitable adhesive known in the art and the light emitting diode 96 is attached to the upper surface of the reflective foil 100 by an electrical conducting adhesive layer 124 and the low pass filter layer 98 is secured to the diode 96 by a light conducting adhesive coating (not shown).

The light emitting diode 96 has associated electrical leads 128 and 130 that extend respectively from the diode 96 and the metal foil 100 located under and in electrical contact with the diode 96 to the respective posts 132 and 134 that are located below the outer under side 114 of the high pass filter layer 78 in a manner similar to that for the leads 58 and 60 and the respective posts 62 and 64 of the embodiment set forth in FIGS. 1 through 3. It will be noted that the light emitting diode 96 and its low pass filter coating or layer 98 is surrounded by the waveguide layer 82 which is cast around the light emitting diode 96 and its low pass filter coating 98 that are centrally located above the center portion of the glass layer 78.

Also, a circular ring shaped machined metal housing 139, that is substantially identical to the metal housing 70 of the embodiment 10, is provided that circles the outer edges of the photodetector layer 74, the filter layer 78, the glass layer 80, the waveguide layer 82 and the indicator layer 94. The lower portion of the machined housing 70 is closed or sealed off with casting ceramic or other potting material 141 known in the art that is identical to the the material 72 of the embodiment 10. This material 141 also secures the posts 102, 104, 132 and 134 in place. Consequently, the sensor 74 is a unitary structure, the same as the sensor embodiment 10. with all its operational components located within the housing 139 and only the positive and negative signal posts 102 and 104 and the electrical power posts 132 and 134 extending from the unitary structure surrounded by and contained within the housing 139. It is important to note, as indicated in FIG. 5, that the light emitting diode 96 and the photodetector 76 are located in such a manner that the primary or main axis of light emission from the light emitting diode 96, designated by the letter C, is substantially perpendicular to the primary or main axis, designated by the letter D, of light detection of the photodetector 76. This is very important for the fluorescence sensor 74 since it it results in high efficiency and high sensitivity.

As illustrated in FIG. 6, the positive post 26 of the sensor 10 is electrically connected to the positive input 140 of a light intensity indicator 142 via the conductor 144, the switch 146 and the conductor 148. In a similar manner, the negative post 28 is electrically connected to the negative input 150 of the light intensity indicator 142 via the conductor 152, the switch 154 and the conductor 156. Alternatively, the sensor 74 can be electrically connected to the light intensity indicator 142 by having the positive post 102 of the sensor 74 connected to the positive input 140 of the light intensity indicator 142 via the conductor 158, the switch 146 and the conductor 148. In a similar manner, the negative post 104 is connected to the negative input 150 of the light intensity indicator 142 via the conductor 160, the switch 154, and the conductor 156. As a result of this arrangement, the light intensity output from either the sensor 10 or 74 can be read on the meter 162 of the light intensity indicator 142 through the use of the switches 146 and 154.

In the preferred embodiments both of the fluorescence sensor embodiments 10 and 74 are manufactured using standard components and techniques known in the art in the following manner. With respect to the fluorescence sensor embodiment 10, the outer housing from a standard optical diode detector such as a UDT020 available from United Detector Technology of Hawthorne, Calif. is removed to expose the surface of the silicon photodiode 12. Onto the upper surface 38 of the diode 12 is placed a small drop of optical adhesive 44 such as manufactured by Norland Products of New Brunswick, N.J. or other similar adhesive. A thin film high pass color filter 14 is die cut from a standard sheet into a circular disc and placed onto the surface 38 of the diode 12 thereby covering the active diode area with the wavelength specific filter that is attached to the surface 38 of the diode 12 by the optical adhesive 44. A suitable film filter 14 may be selected and obtained from any photography lighting supply house such as R & R Lighting Company, Inc. of Silver Spring, Md. Onto the upper surface 46 of the optical film filter disc 14 is placed a second small drop of optical adhesive 50 (Norland type). Onto this surface is placed a circular glass disc 16 of a diameter exceeding that of the color filter 14 and the dimensions of the photodiode detector 12. The glass disc 16 is attached to the upper surface of the colored filter disc 14 by the optical adhesive 50.

Onto the upper surface 52 of the glass disc 16 a small drop 53 of high temperature epoxy, such as that produced by Epoxy Technology, Billercia, Mass., is placed approximately in the center (placement is not critical, but the center is preferred) of the disc 16. A much smaller (approximately 300+ micron) diameter electrically conductive metallic disc 22 is affixed to the glass via the high temperature epoxy 53 and a wire lead 60 (or line of conductive ink or adhesive) is then laid onto the glass layer surface 52 between the metallic disc 22 and a conductive pin or post 64 which is affixed beneath or adjacent to the photodetector which is a photodiode 12 allowing electrical conduction between the post 64 and the centrally located metallic disc 22. Onto the upper surface of the metallic disc 22 is placed a small drop of electrically conductive adhesive 54 such as that made by Circuit Works, Inc. of Santa Cruz, Calif. and others. Onto the conductive adhesive 54 and the associated metallic disc 22 is placed an LED chip emitter die 20 as made by Cree Research, Durham, N.C. and others, thereby forming an electrical path between the post 64 as described previously and the cathode (or anode alternatively) of the LED die 20. Onto the upper surface (anode or cathode) of the LED die 20 one end of a second electrical lead of fine wire 58 is wire bonded and the wire 58 is routed across the surface 52 of the glass disc 16 from the LED die 20 to a second pin or post 62 located adjacent or beneath the photodiode 12. This completes a circuit segment whereby power may be applied across the two posts 62 and 64 thereby energizing the LED die 20 to emit light across the surface of and in radial proximity to the upper surface of the glass disc 16.

This stacked and adhered array comprising the photodetector 12, the filter 14, the glass layer 16, the metal disc 22 and the photodetector 20 and the high pass filter coating 24 is then cemented within a circular housing 70 machined to a dimensioning which covers and protects the array's sides and mates to the periphery of the glass disc 16 with epoxy (Epoxy Technology), thereby hermetically sealing the front face and those components beneath the glass disc 16 from the ambient environment. Into a pocket created by the upper surface 52 of the glass disc 16 and the side wall machined into the housing 70 is poured a membrane indicator formulation 18 (FIG. 1) which covers the surface 52 of the glass layer 16, embeds the LED die 20 and its lead wires 58 and 60 and can fill to a level equal to the thickness machined into the housing 70. The LED 20 is minimally submerged. Due to the formulation of the membrane indicator mixture 18 the liquid self levels across the surface and polymerizes and cures, thereby immobilizing the indicator molecules 71 and forming an active porous membrane as the outer surface on the face of the sensor 10. The membrane thickness can be controlled by precise volumetric dispensing onto the surface 52 of the glass layer 16.

The membrane/indicator formulation may be changed to create different sensors specific for different analytes. In one example embodiment the membrane is formulated and applied as follows to create a sensor specific for oxygen.

Beginning with 1 ml of silicone (commercially available as Dow Corning, Midland, Mich., RTV Sealant) dilute with 2 mls of Naptha (EE Zimmerman Company, Pittsburgh, Pa.) and agitate by vortexing in a sealed glass test tube (13+ cc volume). Add 200 µl of 6 mg/ml fluorescent indicator molecule ruthenium complex dissolved in chloroform. Agitate by vortex to homogeneity and pipette 250 µl of this solution onto the surface of the glass as detailed in the device above. Allow to cure at room temperature over night or in reduced time at higher temperatures (not to exceed 60 degrees Centigrade). The bottom cavity below the underside 34 of the photodetector 12 that is formed by the housing 70 is then filled with the potting material 72 that seals the housing 70 and also secures the various posts 26, 28, 62 and 64 in place.

This example is now ready for use as an oxygen sensor when mated with suitable electronics. Other examples would differ from the description above only by changing the type of indicator molecule 71 and membrane 18 formulation.

As indicated in FIG. 5, the embodiment 74 uses a waveguide layer 82 but is constructed in an identical manner as the embodiment 10 except a non-porous wave guide layer 82 is poured onto the surface 86 of the glass layer 80 instead of a porous membrane of the embodiment 10. There is no indicator molecule within the waveguide layer 80. The indicator molecules 95 are immobilized instead in an indicator layer 94 located on the upper surface 90 of the waveguide layer 80.

As an example of embodiment 74, a clear polymer (organic or inorganic) is poured onto the surface 86 of the glass layer 80 and allowed to self level and cure. The polymer waveguide is chosen for suitable clarity and refractive index properties so as to optimally conduct light of the desired wavelength throughout its volume. The indicator molecule layer 94 is attached to the upper surface 86 of the waveguide layer 82 with the indicator molecules indicated by the number 95 that are immobilized to the upper surface 86 of the waveguide layer 82 using any of dozens of common techniques known in the art, thereby completing the device construction. The specificity of the sensor 10 or 74 for a particular analyte is conferred by the choice of immobilized indicator molecule 71 or 95. Then the optical properties of the waveguide 82 are chosen to accommodate its wavelength optimums.

The sensor embodiments 10 and 74 of this invention are used in the following manner. The sensors 10 and 74 may be used in many different applications and environments. The sensor's analyte specificity is conferred by the indicator molecule 71 or 95 chosen from many available both commercially (SIGMA and others) and as listed in scientific literature.

For example, the sensor 10 or 74 may read oxygen by using many different molecules as listed in the scientific literature and commercially available and known to those skilled in the art. As an oxygen sensor the device may be used to analyze the concentration of dissolved oxygen in a liquid or slurry, i.e. water, chemicals, process streams, fermenter broths, waste treatment streams, etc. or to analyze the oxygen concentration in a gaseous mixture such as air, various gas mixtures containing oxygen utilized in combustion, environmental conditions in enclosed spaces or reactors or life support systems. In one example of many, the previously described sensors 10 and/or 74 is or are connected to electronics comprising a signal amplifier (not shown) from the photodiode detector that can form part of the measuring means for measuring the electric signal from the the photodetector means such as the light intensity indicator 142 and a power supply (not shown) to power the LED 20 or 96. As the sensor 10 or 74 is placed in the environment to be analyzed, oxygen diffuses into the membrane indicator layer 18 or 94 whereby oxygen interacts with the indicator molecules 71 or 95 on a molecular level causing a decrease in fluorescence intensity as detected or seen by the photodetector 12 or 76, thereby decreasing the electronic signal to the processing electronics forming the measuring means 142 for measuring the electric current from the the photodetector means 12 or 76 which is calibrated to read oxygen in suitable units of measure known in the art.

Although the invention has been described in considerable detail with reference to certain preferred embodiments it will be appreciated and understood that various changes and modifications may be made without departing from the spirit and scope of the invention as defined in the appended claims.

What is claimed is:

1. A fluorescence sensor for sensing an analyte comprising: photodetector means for generating an electric signal as a result of being exposed to incident light; indicator means for providing a fluorescent emission as a result of excitation light, said indicator means comprising a material permitting said analyte to diffuse therein and having light emitting indicator molecules specific to said analyte to cause said indicator molecules to interact with said analyte to alter the amount of light incident upon said photodetector means from light emitted from said indicator molecules; light emitting means for emitting excitation light having at least a portion thereof located within said indicator means; said photodetector means having a primary axis of light detection and said light emitting means having a primary axis of light emission, said photodetector means and said light emitting means being located to cause the primary axis of light emission from said light emitting means to be substantially perpendicular to the primary axis of light detection of said photodetector means; said photodetector means, said indicator means and said light emitting means being located in one unitary structure.

2. The fluorescence sensor of claim 1 further comprising filtering means for filtering light located between said indicator means and said photodetector means.

3. The fluorescence sensor of claim 2 wherein said filtering means comprises a high pass filter.

4. The fluorescence sensor of claim 2 wherein said filtering means filters out light above or below a certain wavelength.

5. The fluorescence sensor of claim 2 further comprising second filtering means for filtering light surrounding a portion of said light emitting means.

6. The fluorescence sensor of claim 1 wherein said light emitting means comprises a light emitting diode.

7. The fluorescence sensor of claim 1 wherein said photodetector means has an electric signal output and further comprising measuring means connected to said photodetector means for measuring the electric signal output from said photodetector means.

8. The fluorescence sensor of claim 1 further comprising a housing surrounding at least a portion of said photodetector means, said indicator means and said light emitting means.

9. The fluorescence sensor of claim 1 further comprising a glass layer located adjacent to said indicator means.

10. The fluorescence sensor of claim 1 wherein said indicator means comprises a substantially flat indicator membrane.

11. The fluorescence sensor of claim 1 wherein the light emitting indicator molecules of said indicator means interact with oxygen.

12. A fluorescence sensor for sensing an analyte comprising: photodetector means for generating an electric signal as a result of being exposed to incident light; indicator means for providing a fluorescent emission as a result of excitation light, said indicator means comprising a material permitting said analyte to diffuse therein and having light emitting indicator molecules specific to said analyte to cause said indicator molecules to interact with said analyte to alter the amount of light incident upon said photodetector means from light emitted from said indicator molecules; a waveguide layer located adjacent to said indicator means; light emitting means for emitting excitation light having at least a portion thereof surrounded by said waveguide layer; said photodetector means having a primary axis of light detection and said light emitting means having a primary axis of light emission, said photodetector means and said light emitting means being located to cause the primary axis of light emission from said light emitting means to be substantially perpendicular to the primary axis of light detection of said photodetector means; said photodetector means, said indicator means, said waveguide layer and said light emitting means being located in one unitary structure.

13. The fluorescence sensor of claim 12 further comprising filtering means for filtering light located between said said waveguide layer and said photodetector means.

14. The fluorescence sensor of claim 13 wherein said filtering means comprises a high pass filter.

15. The fluorescence sensor of claim 13 further comprising second filtering means for filtering light surrounding a portion of said light emitting means.

16. The fluorescence sensor of claim 12 wherein said light emitting means comprises a light emitting diode.

17. The fluorescence sensor of claim 12 wherein said photodetector means has an electric signal output and further comprising measuring means connected to said photodetector means for measuring the electric signal output from said photodetector means.

18. The fluorescence sensor of claim 12 further comprising a housing surrounding at least a portion of said photodetector means, said indicator means and said waveguide layer.

19. The fluorescence sensor of claim 12 further comprising a glass layer located adjacent to said waveguide layer.

* * * * *